United States Patent
Wang et al.

(10) Patent No.: US 10,443,041 B2
(45) Date of Patent: Oct. 15, 2019

(54) METHOD FOR ACTIVATING AND EXPANDING NKT-LIKE CELLS IN VITRO

(71) Applicant: Beijing Zhongtai Hengji Biological Technology Co., Ltd., Beijing (CN)

(72) Inventors: Chao Wang, Beijing (CN); Zhengyuan Li, Beijing (CN)

(73) Assignee: Beijing Zhongtai Hengji Biological Technology Co., Ltd., Beijing (CN)

( * ) Notice: Subject to any disclaimer, the term of this patent is extended or adjusted under 35 U.S.C. 154(b) by 131 days.

(21) Appl. No.: 15/632,944

(22) Filed: Jun. 26, 2017

(65) Prior Publication Data

US 2018/0002665 A1   Jan. 4, 2018

(30) Foreign Application Priority Data

Jun. 29, 2016  (CN) .......................... 2016 1 0497248

(51) Int. Cl.
*C12N 5/0783* (2010.01)

(52) U.S. Cl.
CPC ........ *C12N 5/0646* (2013.01); *C12N 2501/20* (2013.01); *C12N 2501/2302* (2013.01); *C12N 2502/03* (2013.01); *C12N 2502/1121* (2013.01)

(58) Field of Classification Search
None
See application file for complete search history.

(56) References Cited

U.S. PATENT DOCUMENTS 10,149,863 B2 * 12/2018 Zhang .................... A61K 35/17

OTHER PUBLICATIONS

Vallee et al., J Immunol. Aug. 15, 1998;161(4):1652-1658 (Year: 1998).*
Ralph C. Budd; Brief Definitive Report; Developmentally Regulated Expression of T Cell Receptor β Chain Variable Domains in Immature Thymocytes; Aug. 1, 1987.
B. J. Fowlkes; Letters to Nature, vol. 329; A Novel Population of T-Cell Receptor αβ-Bearing Thymocytes which Predominantly Expresses a Single $V_\beta$ Gene Family; Sep. 17, 1987.
Rhodri Ceredig; Proc. Natl. Acad. Sci. USA; vol. 84, pp. 8578-8582; Phenotypic Properties, Interleukin 2 Production, and Developmental Origin of a "Mature" Subpopulation of Lyt-2⁻ L3T4⁻ Mouse. Thymocyes; Dec. 1987.
M Sykes; The Journal of Immunology; Unusual T Cell Populations in Adult Murine Bone Marrow. Prevalence of CD3+CD4-CD8 and Alpha Beta TCR+NK1.1+Cells; Jul. 7, 2016.
Yasuhiko Makino; International Immunology, vol. 7, No. 7, pp. 1157-1161; Predominant Expression of Invariant $V_\alpha$ 14⁺ TCR α Chain in NK1.1⁺ T Cell Popluations; Apr. 6, 1995.
Dale I. Godfrey; Nature Publishing Group, vol. 4; NKT Cells: What's in a Name?; Mar. 2004.
Motoi Maeda; The Journal of Immunology; CD1d-Independent NKT.
Cells in $\beta_2$-Microglobulin-Deficient Mice Have Hybrid Phenotype and Function of NK and T Cells; Jul. 7, 2016.

* cited by examiner

*Primary Examiner* — Daniel C Gamett
(74) *Attorney, Agent, or Firm* — The Dobrusin Law Firm, PC

(57) ABSTRACT

The invention relates to a method for activating and expanding NKT-like cells in vitro. The method according to the present invention utilizes nucleated somatic cells derived from allogeneic or heterologous subjects to activate and proliferate NKT-like cells of a subject in vitro, and can increase the overall number of the NKT-like cells, the expression of activation markers and the number of killing effector molecules.

12 Claims, 5 Drawing Sheets

METHOD FOR ACTIVATING AND EXPANDING NKT-LIKE CELLS IN VITRO

CROSS REFERENCE TO RELATED APPLICATIONS

The present application is based on, and claims priority from CN Application No. 201610497248.2, filed on Jun. 29, 2016, the disclosure of which is incorporated by reference herein in its entirety.

TECHNICAL FIELD

The present invention relates to a method for activating and expanding NKT-like cells in vitro, specifically, a method for activating and expanding a CD 8+ NKT-like cell subpopulation in lymphocytes of a mammal subject in vitro by utilizing nucleated somatic cells derived from allogeneic or heterologous subjects.

BACKGROUND

In 1987, three independent research teams reported a population of T cells expressing a moderate intensity of TCRαβ and having no expressions of CD4 and CD8[1-3], respectively; in 1990, Sykes reported a cell subpopulation which expresses both NK1.1 and TCRαβ[4]. In 1995, "NKT" cell was firstly used as a proper noun, and it especially refers to a subpopulation of T cells expressing NK1.1 (mouse, CD161c) marker[5]. According to the CD1d restriction and the TCR diversity of NKT cells, Godfrey classified mouse NKT cells into three types of populations: Type I NKT cells, Type II NKT cells and NKT-like cells. Type I NKT cells were classified as a population of NKT cells that can recognize CD1d presented α-Galcer lipid antigens. Type II NKT celsl can recognize CD1d presented lipid antigens other than α-Galcer. NKT-like cells include other NKT cell subpopulations other than Type I NKT cells and Type II NKT cells. Among them, most extensive researches have been made on the immunological features and functions of the Type I NKT cell which is also known as a classical NKT cell; at present, most of NKT cells mentioned in the literatures are actually the classical NKT cells. With the development of CD1d tetramer technology as well as the establishment of CD1d-deficient transgenic mice, the current researches on NKT cells mostly focused on the classical NKT cell (i.e., Type I NKT cell). However, Type I NKT cell is only one population of NKT cell, and more than 50% of NKT cells are NKT-like cells[6]. The development of NKT-like cell does not depend on CD1d molecules, and yet NKT-like cell expresses a variety of TCR chains. However, there are few researches on the NKT-like cells at present. Existing researches showed that the NKT-like cells have an antitumor effect. A population of NKT-like cells which is not dependent on CD1d molecules has been found in β2 microglobulin deficient mice, and these cells can be able to kill many kinds of tumor cells in vitro[7].

Chinese patent application No. 201510494011.4 relates to a new NKT-like cell subpopulation and use thereof in the treatment of tumor. The NKT-like cell subpopulation comprises CD8+ NKT-like cells which were demonstrated as cells having a potent anti-tumor effect in NKT-like cells. In the application, the autologous lymphocytes were isolated from a subject and then NKT-like cell subpopulation was sorted out from the lymphocytes. The sorted NKT-like cell subpopulation was expanded by the addition of a cytokine or a combination of cytokines. The expansion of sorted CD8+ NKT-like cells was achieved by the addition of a specific cytokine or a specific combination of cytokines in CN 201510494011.4. However, the application did not mention other means or possibilities of the activation and expansion of CD8+ NKT-like cells in vitro.

SUMMARY

After extensive studies, the present inventor has surprisingly found that an in vitro co-culture of lymphocytes derived from a subject and nucleated somatic cells derived from another subject can not only significantly increase the number of CD8+ NKT-like cells in the lymphocytes, and can also trigger the expression of activation markers (such as CD25, CD44, CD69) and lead to the increase of killing effector molecules (Granzyme B, Perforin).

Accordingly, an object of the present invention is to provide a method for activating and expanding NKT-like cells in vitro (hereinafter sometimes referred to simply as "the method of the present disclosure"), which comprises the steps of: 1) providing and culturing lymphocytes obtained from a first subject; 2) providing nucleated somatic cells obtained from a second subject; 3) adding the nucleated somatic cells of the second subject to the culture of the lymphocytes of the first subject, and continuously culturing the resulting mixed culture for a period sufficient to expand the number of the lymphocytes by at least 10 to 1000 times; and 4) sorting out NKT-like cells or a subpopulation rich in NKT-like cells from the lymphocytes; wherein the NKT-like cells express CD8 molecule on their cell surface (hereinafter sometimes referred to simply as "CD8+ NKT-like cells"), and the nucleated somatic cells express immune co-stimulatory molecules; the second subject and the first subject are allogeneic or heterogeneous mammals.

In one embodiment, the lymphocytes of the first subject and the nucleated somatic cells of the second subject may express different types of MHC class I molecules.

In one embodiment, the nucleated somatic cell may be an immune cell or a non-immune cell.

In a preferred embodiment, the non-immune cell may be a fibroblast.

In another preferred embodiment, the immune cell may be an antigen presenting cell, and the antigen presenting cell may be any one selected from the group comprising an endothelial cell, a dendritic cell and a B cell, preferably a dendritic cell.

In another preferred embodiment, the immune cell may be any one selected from the group comprising a granulocyte, a T cell, a B cell, a macrophage, a NK cell, a NKT cell and a NKT-like cell, preferably a macrophage, a B cell or a NKT-like cell.

In one embodiment, the CD8+ NKT-like cell may express CD3 and CD56 (or CD161c) on their cell surface, but not Vα24 TCR. The CD8+ NKT-like cell may also express TCRαβ on their cell surface.

In a preferred embodiment, the second subject and the first subject may be semi-allogeneic individuals.

In another embodiment, the second subject and the first subject may be heterogeneous individuals.

In another embodiment, prior to the step 3) of the method of the present invention, the nucleated somatic cells of the second subject obtained in the step 2) may be incubated with a tumor antigen so that the nucleated somatic cells phagocytose the tumor antigen.

In another embodiment, the nucleated somatic cells of the second subject obtained in the step 2) may be subjected to any one selected from the following treatments: heat inactivation, radiation inactivation, chemical reagent fixation, frozen treatment and ultrasonic cleavage treatment.

In one embodiment, prior to the step 3) of the method of the present invention, cytokines may be added to the culture of the nucleated somatic cells obtained in step 2) to expand or activate the nucleated somatic cells.

In another embodiment, in the step 3) of the method of the present invention, the nucleated somatic cells may be added to the culture of the lymphocytes at a ratio of nucleated somatic cells to lymphocytes of 1:1000 to 1:1, preferably 1:100 to 1:1, more preferably 1:10 to 1:1, and most preferably 1:1.

In another embodiment, the method of the invention may further comprise: adding a cytokine capable of stimulating T cell proliferation and activation to a culture of the NKT-like cell subpopulation sorted out in the step 4) of the method of the invention, thereby further expanding the NKT-like cells by 10 to 1000 times.

The method of the present invention is simpler and more efficient than the method of activation and expansion described in CN 201510494011.4, not only omitting the steps of adding cytokines into the culture system, but also more easily activating and expanding $CD8^+$ NKT-like cells in vitro on a large scale, further leading to the expression of activation markers (such as CD25, CD44, CD69) and the increase of killing effector molecules (Granzyme B, Perforin), thereby enhancing the biological effects of $CD8^+$ NKT-like cells, such as an antitumor effect.

Some aspects, advantages, and novel features have been described in the above summary. However, it is to be understood that not necessarily all such advantages will be embodied in any particular embodiment of the invention. Therefore, those skilled in the art will appreciate that the present invention can be practiced or performed by means of a combination of one or more advantages as taught herein, and not necessarily achieve other or all advantages as taught or set forth herein.

DESCRIPTION OF DRAWINGS

With reference to the following drawings, the preferred embodiments of the disclosure will be illustrated, and the above and other features, aspects and advantages of the disclosure will be described in more detail. It will be appreciated that the exemplary embodiments are intended to illustrate rather than limit the invention. In the drawings:

In FIG. 1, the black line denotes molecular expression level, and the gray line denotes the expression level of corresponding isotype control.

In FIG. 2, hollow area denotes the expression level of specified molecules, and the fill area denotes the expression level of corresponding isotype control.

DETAILED DESCRIPTION

Figure 1:
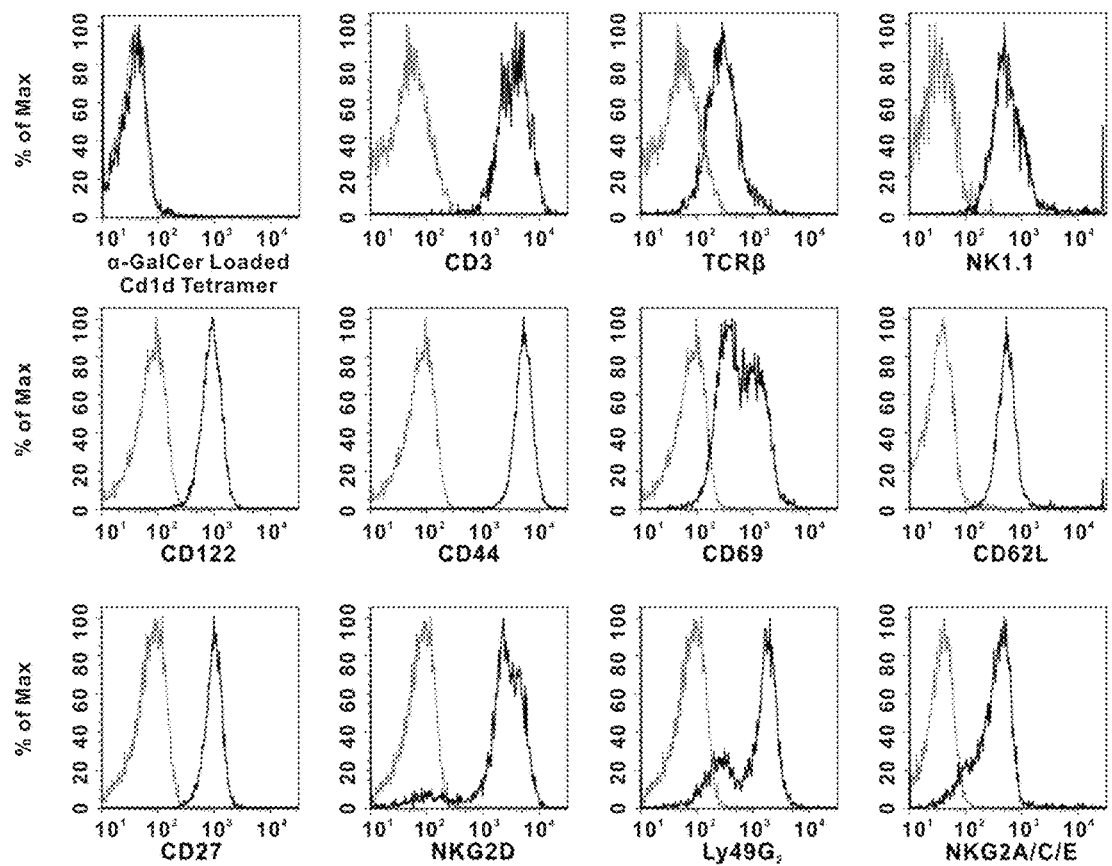
FIG. 1 illustrates the phenotype of the mouse $CD8^+$ NKT-like cells disclosed herein.

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods, and materials are now described. All publications and patent applications cited herein are incorporated herein by reference in their entirety. Nothing herein is to be construed as an admission that the invention is not entitled to antedate such disclosure by virtue of prior invention.

It must be noted that as used herein and in the appended claims, the singular forms "a," "an," and "the" include plural references unless the context clearly dictates otherwise.

Definitions

As used herein, the term"NKT cell" has two definitions in broad sense and narrow sense. The NKT cell in broad sense refers to a cell population expressing both NK cell surface marker (CD161c in mouse, and CD 56 in human) and T cell surface markers. With the development of lipid antigen bound CD1d tetramer technology, researchers have found a cell subpopulation capable of binding CD1d tetramers loaded with lipid antigen α-GalCer in mice, the majority of cells in the subpopulation expressing both NK cell surface marker and T cell surface markers. Such cell subpopulation secretes a great amount of cytokines and has an immunomodulatory activity; according to Godfrey definition, this population of cells was classified as the type I NKT cell, namely, NKT cell in narrow sense. At present, most extensive and most thorough researches have been made on this population of cells and thus this population of cells is also known as a classical NKT cell. The NKT cell mentioned in literatures mainly is the NKT cell in narrow sense. In the disclosure, unless explicitly specified, the NKT cell refers to the NKT cell in broad sense for all purpose.

As used herein, the term "iNKT cell", namely, NKT cell in narrow sense, is also known as invariant NKT cell (sometimes referred to as iNKT cell herein)[7], owing to the fact that the subpopulation expresses invariant TCR chain (Vα14Jα18 in mouse, Vα24Jα18 in human).

The term "the NKT-like cell" as used herein refers to a cell subpopulation expressing both NK cell surface marker (CD161c in mouse, CD56 in human) and T cell surface markers (for example, TCR and/or CD3) with its development independent on CD1d molecule. This population of cells is characterized that the surface of individual cell may express different types of TCR respectively. However, this population of cells does not include the cells expressing Vα24 TCR (human) or Vα14 TCR (mouse)[7]. The definition of this population of cells is opposed to those of classical NKT cell or NKT cell in narrow sense (in terms of Vα24 TCR or Vα14 TCR).

The term "Vα24 TCR" as used herein refers to TCR sequence that expresses Vα24 gene. According to classical immunology theory, the rearrangement of TCR sequence is considered to result in the diversity of TCR sequence of T cells, while some cell subpopulations having special TCR preferentially express certain type of TCR sequence. For example, the classical NKT cell preferentially expresses Vα24 TCR. The definition of "Vα14 TCR" is similar to that of "Vα24 TCR".

The term "CD1d restricted" as used herein refers to the dependence of development of immune cells on CD1d molecule. In populations of NKT cells, the classical NKT cells are considered to be CD1d restricted, and NKT-like cells are considered to be non-CD1d restricted.

The term "CD8+" as used herein means that CD8 marker is expressed on the cell surface.

The term "tumor antigen" as used in the present disclosure refers to a molecule that expresses on tumor cells due to the gene mutations of the tumor cells and does not express on normal tissue cells.

The term "semi-allogeneic" as used in the present disclosure refers to "haploidentical". In the present disclosure, "the second subject and the first subject are semi-allogeneic individuals" means that the second subject has a direct phylogenetic relationship with the first subject, i.e., a relative semi-allogeneic relationship. For example, in the case of human, the second subject may be the parent, children or sibling of the first subject.

CD8+ NKT-like Cells

Unless otherwise specifically stated, NKT-like cells as used in the present disclosure refer to CD8+ NKT-like cells.

According to some embodiments, the CD8+ NKT-like cells may express CD3 and CD56 (or CD161c), but not Vα24 TCR (Vα14 TCR), namely that, its phenotype may be denoted as CD3+CD56+CD8+Vα24 TCR− or CD3+CD161c+CD8+Vα14 TCR−.

In a specific embodiment, the CD8+ NKT-like cell may also express TCRαβ on its surface, that is, its phenotype may be denoted as TCRαβ+CD3+CD56+CD8+Vα24 TCR− or TCRαβ+CD3+CD161c+CD8+Vα14 TCR−.

FIG. 1 illustrates the phenotype of the CD8+ NKT-like cells. In FIG. 1, it can be seen that the mouse CD8+ NKT-like cells express T cell lineage marker CD3 and TCRβ as well as NK cell lineage marker NK1.1 (CD161c), but do not express iNKT lineage marker CD1d. In addition, it also can be seen from FIG. 1 that the CD8+ NKT-like cells express T cell activation markers (CD44. CD62L and CD122) as well as NK cell receptors (NKG2A/C/E, NKG2D, Ly49G2 and CD27). These results indicate that these cells have the functional characteristics of both NK cells and T cells.

Figure 2:
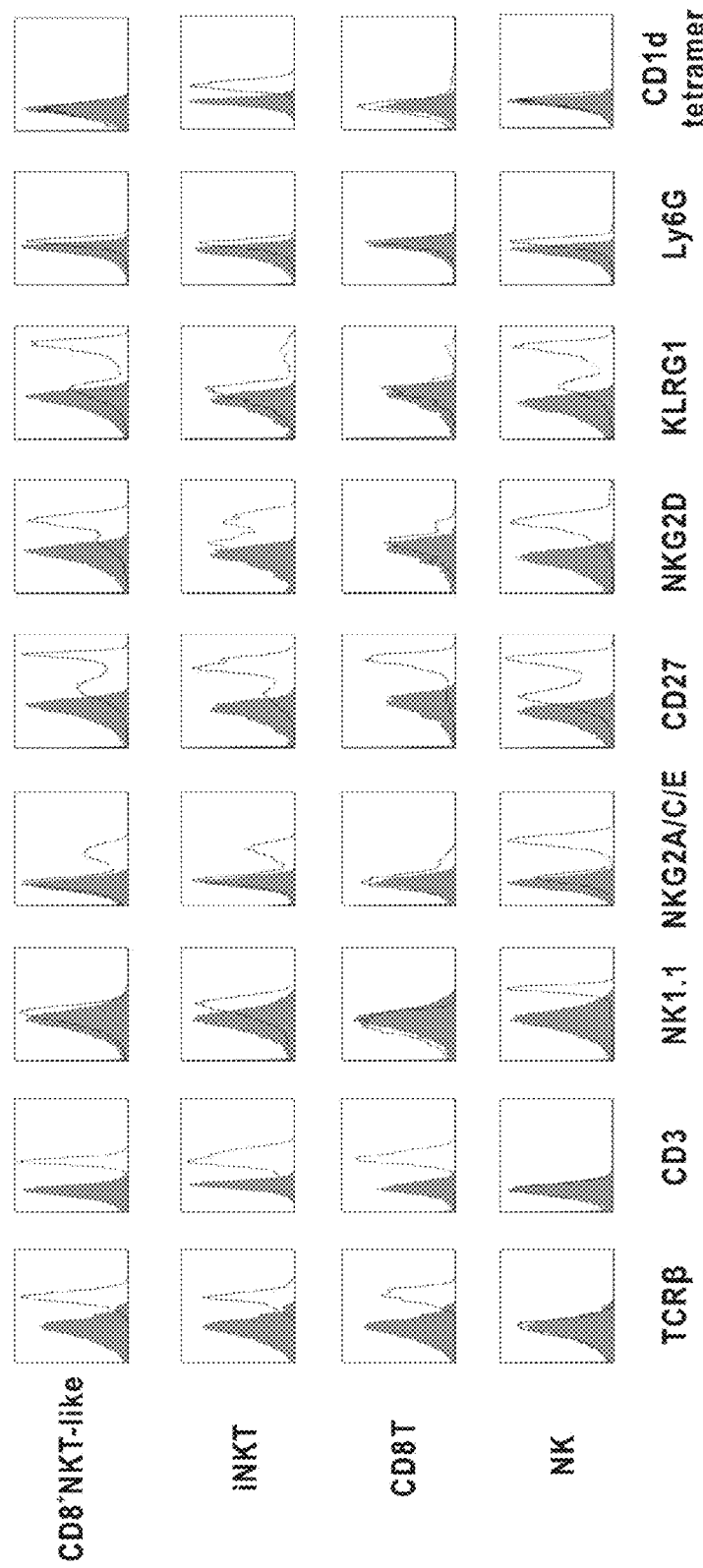
FIG. 2 illustrates the phenotypic differences between the mouse $CD8^+$ NKT-like cells disclosed herein and mouse NK cells, mouse iNKT cells and mouse CTL cells.

FIG. 2 shows the phenotypic differences between the mouse CD8+ NKT-like cells and NK cells, iNKT cells and CTL cells. It can be seen from FIG. 2 that: (1) compared with NK cells, the mouse CD8+ NKT-like cells express not only NK cell markers [NK1.1 (CD161c), NKG2A/C/E, CD27, and Ly6G], but also TCRβ and CD3 which are not expressed on the NK cells; (2) compared with CTL cells, the mouse CD8+ NKT-like cells express T cell lineage markers (TCRβ and CD3), but do not express NK cell receptors; (3) compared with iNKT cells, the CD8+ NKT-like cells cannot bind to the CD1d tetramer loaded with lipid antigens. These results indicate that the CD8+ NKT-like cell disclosed herein is a new immune cell subpopulation which is distinct from any one of the existing immune cell subpopulations having defined phenotypes in the prior art.

Table 1 shows the phenotypic differences between mouse CD8+ NKT-like cells and NK cells, iNKT cells and CTL cells.

|  | CD8+NKT-like cell | NK cell | CTL cell | iNKT cell |
| --- | --- | --- | --- | --- |
| CD3 | + | − | + | + |
| TCRβ | + | − | + | + |
| NK1.1 | + | + | − | + |
| CD1d tetramer | − | − | − | + |
| CD69 | + | + | + | + |
| NKG2A/C/E | + | + | − | + |
| CD27 | + | + | + | + |
| NKG2D | + | + | − | + |

Table 1 shown above summarizes the results of FIG. 2 in a table format. From Table 1, the phenotypic differences between mouse CD8+ NKT-like cells and NK cells, iNKT cells and CTL cells are clearly shown.

Method for Activating and Expanding the NKT-like Cells In Vitro

The disclosure provides a method for activating and expanding CD8+ NKT-like cells in vitro, which comprises the steps of: 1) providing and culturing lymphocytes obtained from a first subject; 2) providing nucleated somatic cells obtained from a second subject; 3) adding the nucleated somatic cells of the second subject to the culture of the lymphocytes of the first subject, and continuously culturing the resulting mixed culture for a period sufficient to expand the number of the lymphocytes by at least 10 to 1000 times; and 4) sorting out NKT-like cells or a subpopulation rich in NKT-like cells from the lymphocytes.

In the disclosure, both the first subject and the second subject may be a mammal. The mammal may be selected from the species such as bovidae, equidae, felidae, canidae, leporidae, suidae, camelidae, rodent and primate, including but not limited to, a cattle, a horse, a goat, a sheep, a cat, a rabbit, a pig, a camel, an alpaca, a rat, a mouse, a guinea pig and a non-human primate (such as ape, monkey, baboon, orangutan) or a human, preferably a cattle, a horse, a dog, a goat, a sheep, a pig, a camel, a rat, a mouse, a monkey or a human, more preferably a human.

In the present disclosure, the first and second subjects may be allogeneic or xenogenic individuals. For example, if the first subject is a mouse, the second subject may be a mouse (of a same strain or a different strain); if the first subject is a mouse, the second subject may be any one mammal selected from the above that is not a mouse, such as a rat. Preferably, the second subject may be a haploidentically allogeneic mammal of the first subject.

In the present disclosure, it is particularly preferred for the first subject that the second subject is a haploidentically allogenic individual. In this case, since the same haploid as the first subject is retained, the nucleated somatic cells obtained from the second subject, especially DCs and B cells, can induce the activation of specific and nonspecific CD8+ NKT-like cells as well as specific and nonspecific CTLs in the first subject respectively, further enhancing bidirectional inhibition of tumor cells in vivo. While in the case of unmatched allogeneic or xenogenic individuals, the nucleated somatic cells obtained from the second subject may only induce the activation of nonspecific CD8+ NKT-like cells as well as nonspecific CTLs.

Unless specifically indicated, the above description and definition of mammal is applicable to all sections, paragraphs, any one embodiment, examples and claims that recite the mammal herein.

In the method of in vitro expanding CD8+ NKT-like cells of the disclosure, the method of obtaining lymphocytes is not particularly limited, and the methods well-known in the art, for example, density gradient centrifugation and the like, may be employed.

In the method of the present disclosure, the method of culturing lymphocytes is not limited, and the culture methods known in the art and corresponding culture medium, steps and culture conditions may be used.

According to the present disclosure, the nucleated somatic cells may express immune co-stimulatory molecules, such as CD40, CD80, CD86 molecules, that can be capable of sufficiently activating CD8+ NKT-like cells.

In a preferred embodiment, the lymphocytes of the first subject and the nucleated somatic cells of the second subject may express different MHC class I molecules. For instance, MHC class I molecule in the first subject may be HLA-A * 0203, and the MHC class I molecular in the second subject may be HLA-A * 0206.

In a preferable embodiment, in the step 3) of the method of the present disclosure, the nucleated somatic cells may be added to the culture of the lymphocytes at a ratio of nucleated somatic cells to lymphocytes of 1:1000 to 1:1, preferably 1:100 to 1:1, more preferably 1:10 to 1:1, and most preferably 1:1.

In another embodiment, in the step 3), interleukin 2 (IL-2) may be added to the co-culture system of the nucleated somatic cells and the lymphocytes at a final concentration of 50 IU to 5000 IU/ml.

In the method of the present disclosure, in the step 3), after the co-culture system of the nucleated somatic cells and the lymphocytes is cultured for 7 to 30 days, the number of in vitro activated CD8+ NKT-like cells may be increased by 10 to 1000 times in the co-culture system.

The cell sorting technique used in the method of the disclosure is well-known in the art, and can be accomplished by using the method or equipment commonly used in the art, without any limitation in the disclosure. Any technologies, methods and equipment that are used to sort cells may be employed in the disclosure, as long as the surface markers are used to sort cells in these technologies, methods and equipment. For example, a magnetic sorting technique or a flow cytometry can be used. The experimental processes of the cell sorting technique such as a magnetic separation technique or a flow cytometry can be found in various scientific literatures, or may be performed according to instructions or recommended protocols provided by the manufacturer of the equipment or instrument. A person skilled in the art would have the ability to obtain these specific experimental processes or protocols.

With regard to the surface markers, a single marker or a combination of two or more markers may be selected according to the species of the subject (e.g., human, mouse, dog, etc.) and the range of the proportion of target cells to be isolated and enriched in the final isolated cells (e.g., 50%, 60%, 70%, 80%, 90% or more). For example, a combination of CD3, CD56, CD8 and Vα24 TCR may be selected for the sorting of human CD8+ NKT-like cells, and a combination of CD3, CD56, CD8, Vα24 TCR and TCRαβ (that is, sorting out TCRαβ+CD3+CD56+CD8+Vα24 TCR−NKT− like cells) is used so as to achieve a higher enrichment ratio by adding a marker, TCRαβ to the combination. Furthermore, a combination of CD3, CD161c, CD8 and Vα14 TCR may be selected for the sorting of mouse NKT-like cells, and a combination of CD3, CD161c, CD8, Vα14 TCR and TCRαβ (that is, sorting out TCRαβ+CD3+CD161c+CD8+Vα14 TCR−NKT− like cells) is used so as to achieve a higher enrichment ratio by adding a marker, TCRαβ to the combination.

The culture condition of the CD8+ NKT-like cells is not particularly limited in the present disclosure. Culture media routinely used for T cell culture, such as RPMI-1640 culture medium, may be employed. The conditions commonly used for culturing T cells may be employed, for example, at 37° C., 5% $CO_2$, and changing culture medium every 3 to 5 days.

If the sorted CD8+ NKT-like cells do not reach the required number, the cytokines that can be able to stimulate T cell proliferation and activation may be added to the culture of CD8+ NKT-like cell subpopulation. The cytokines that can be able to stimulate T cell proliferation and activation include, but not limited to, GM-CSF, IL-2, IL-4, IL-5, IL-6, IL-7, IL-9, IL-12, IL-15 and 4-1BBL, and the like, and any one of these mentioned cytokines or any combination thereof may be used.

CN 201510494011.4 demonstrated that CD8+ NKT-like cells have an anti-tumor effect which is stronger than that of NK cells and the classical anti-tumor effect elicited by CTLs, and are capable of negatively regulating immune response in both antigen-specific and non-antigen-specific manners. Thus, in a preferred embodiment, the nucleated somatic cells of the second subject obtained in step 2) of the present method may be incubated with tumor antigens prior to step 3) such that the nucleated somatic cells phagocytose the tumor antigen(s) and thus the CD8+ NKT-like cell subpopulation in the activated nucleated somatic cells will gain a specific killing ability against the tumor antigen(s) after co-incubated with the lymphocytes of the first subject, thereby giving the CD8+ NKT-like cells an antigen-specific anti-tumor ability. For example, Her2 molecule expressed in tumor tissue of some breast cancer patients may be firstly incubated with the nucleated somatic cells of the second subject, and then the lymphocytes of the first subject are stimulated by the resulting nucleated somatic cells, thereby obtaining a CD8+ NKT-like cell subpopulation having a specific killing action against the tumor antigen.

The Nucleated Somatic Cells of the Second Subject

In the present disclosure, the nucleated somatic cell may be an immune cell or a non-immune cell. Preferably, the non-immune cell may be a fibroblast. Preferably, the immune cell may be an antigen presenting cell, and the antigen presenting cell may be any one selected from the group comprising an endothelial cell, a dendritic cell and a B cell, preferably a dendritic cell. The immune cell may be any one selected from the group comprising a granulocyte, a T cell, a B cell, a macrophage, a NK cell, a NKT cell and a NKT-like cell, preferably a macrophage, a B cell or a NKT-like cell. The methods of collecting and separating these cells may employ the methods and procedures commonly used in the art.

The nucleated somatic cells obtained from the second subject may be any one selected from the group comprising the nucleated somatic cells freshly isolated from the second subject, the established cell line obtained after a long-term culture of the nucleated somatic cells isolated from the second subject, or the cell population obtained after the expansion or activation by adding cytokines (growth factors or activating factors, as detailed below) to the culture system of the nucleated somatic cells freshly isolated from the second subject.

Thus, in a preferred embodiment, a cytokine or cytokines may be added to the cultures of the nucleated somatic cells obtained in the step 2) of the method of the present disclosure prior to the step 3) so as to expand or activate the nucleated somatic cells. The above-mentioned cytokine(s) may be selected from the group consisting of growth factors such as fibroblast growth factor, endothelial cell growth factor, granulocyte/monocyte colony stimulating factor, or activating factors such as tumor necrosis factor alpha, or any combination thereof.

As a specific example, the following combination of cytokines may be added: 0.1 to 10 ng/ml of fibroblast growth factor (FGF), 0.01 to 1 ng/ml of endothelial cell growth factor (EGF), 1 to 1000 ng/ml of granulocyte/monocyte colony stimulating factor, 0.1 to 100 ng/ml of interleukin 4 (IL-4), 0.1 to 100 ng/ml of interleukin 6 (IL-6), 0.1 to 10 ng/ml of lipopolysaccharide (LPS), 1 to 100 ng/ml of tumor necrosis factor alpha (TNF-α). It is to be understood that the specific example described above are provided only for the purpose of illustration and are not intended to limit the scope of the invention in any way.

In the present disclosure, the nucleated cells may also be prepared as a cell preparation which is convenient for storage and repeated usage. Specifically, after the nucleated cells of the second subject are obtained in step 2) of the present method, the nucleated cells may be subjected to the following treatments: heat inactivation, radiation inactivation, chemical reagent fixation, frozen treatment and ultrasonic cleavage treatment.

Figure 3:
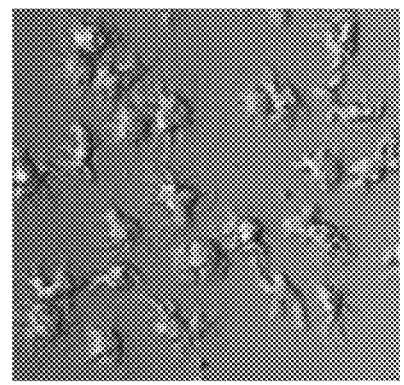
FIG. 3 illustrates a photomicrograph of mouse dendritic cells cultured in vitro for 7 days.

FIG. 3 illustrates the morphology of mature dendritic cells obtained by culturing a culture of the nucleated somatic cells obtained in Example 3 (mainly hematopoietic precursor cells in bone marrow) for 7 days after the addition of several cytokines. The added cytokines include 100 ng/ml of granulocyte/monocyte colony stimulating factor (GM-CSF), 50 ng/ml of interleukin 4 (IL-4), 50 ng/ml of tumor necrosis factor alpha (TNF-alpha). It can be seen from FIG. 3, the morphology of mature dendritic cell was characterized by abundant, long dendrites, and a smaller cell body.

Figure 4:
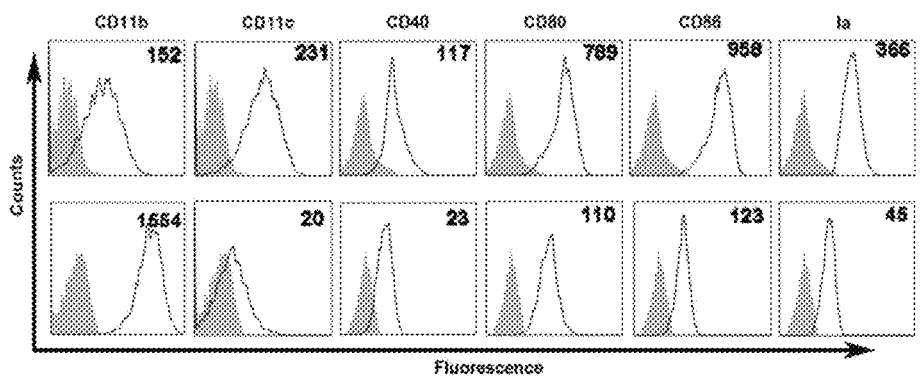
FIG. 4 illustrates the phenotypic detection results of the mouse dendritic cells cultured in vitro for 7 days. Light gray denotes the fluorescence intensity of an isotype control, black denotes the fluorescence intensity of the measured sample.

FIG. 4 illustrates the immunological phenotype of mouse mature dendritic cells. As can be seen from FIG. 4, the expression of CD11c, CD40, CD80, CD86, and Ia on mature mouse dendritic cells was higher than immature dendritic cells. The result indicates that the above molecular markers can be used as the markers of mouse mature dendritic cells.

In Vitro Activation and Expansion of $CD8^+$ NKT-like Cells

Figure 5:
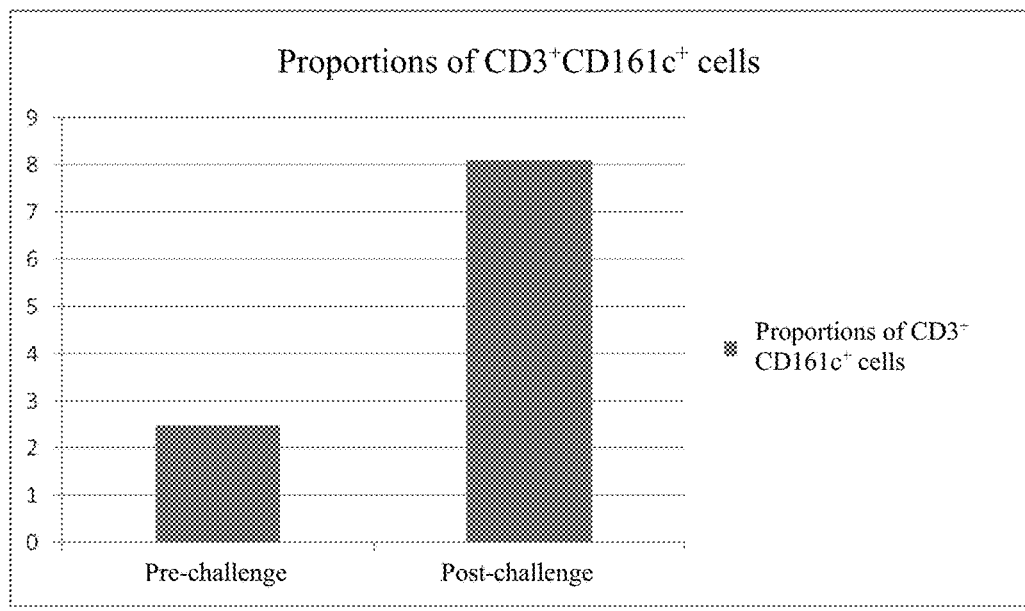
FIG. 5 illustrates the change of the proportions of $CD3^+$ $CD161c^+$ cells in the culture system of the mouse spleen cells after challenged by allogeneic (mouse) nucleated somatic cells (dendritic cells) in vitro.

FIG. 5 illustrates the change of the proportions of $CD3^+CD161c^+$ cells in the culture system of the mouse spleen cells after challenged by allogeneic (mouse) nucleated somatic cells (dendritic cells) in vitro. Dendritic cells of allogeneic mice (DBA mice) were added to C57BL/6 mouse lymphocytes according to the procedure of Example 5. The percentage of $CD3^+CD161c^+$ cells in the cell subpopulation was measured on day 14 of culture. It can be seen from FIG. 5 that the addition of allogeneic dendritic cells (shown as "post-challenge" in the Figure) can efficiently promote the increase in the proportion of $CD8^+$ NKT-like cells compared to the proportion prior to challenge (shown as "pre-challenge" in the Figure).

Figure 6:
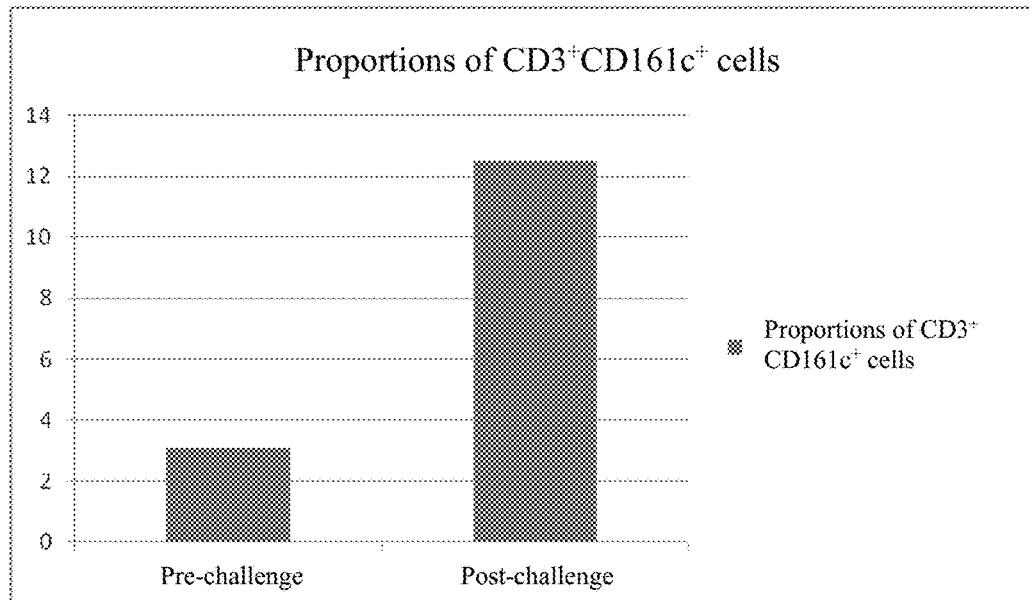
FIG. 6 illustrates the change of the proportions of $CD3^+$ $CD161c^+$ cells in the culture system of the mouse spleen cells after challenged by xenogeneic (rat) nucleated somatic cells (peritoneal macrophages) in vitro.

FIG. 6 illustrates the change of the proportions of $CD3^+CD161c^+$ cells in the culture system of the mouse spleen cells after challenged by xenogeneic (rat) nucleated somatic cells (peritoneal macrophages) in vitro. Xenogeneic (rat) peritoneal macrophages were added to C57BL/6 mouse lymphocytes according to the procedure of Example 6. The percentage of $CD3^+CD161c^+$ cells in the cell subpopulation was measured on day 14 of culture. It can be seen from FIG. 6 that the addition of xenogeneic peritoneal macrophages (shown as "post-challenge" in the Figure) can efficiently promote the increase in the proportion of $CD8^+$ NKT-like cells compared to the proportion prior to challenge (shown as "pre-challenge" in the Figure).

Figure 7:
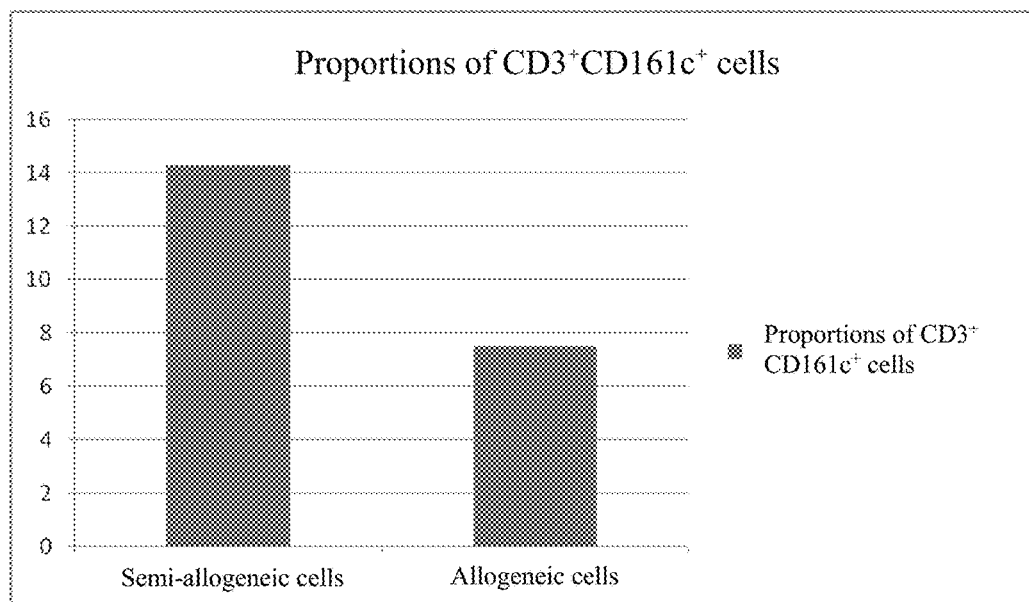
FIG. 7 illustrates the change of the proportions of $CD3^+$ $CD161c^+$ cells in the culture system of the mouse spleen cells after challenged by semi-allogeneic mouse dendritic cells and common allogeneic dendritic cells in vitro.

FIG. 7 illustrates the change of the proportions of $CD3^+CD161c^+$ cells in the culture system of the mouse spleen cells after challenged by semi-allogeneic mouse dendritic cells and common allogeneic dendritic cells in vitro. According to the procedure of Example 7, the allogeneic (DBA mice) or semi-allogeneic (F1 hybrid mice of C57BL/6 mice and DBA mice) dendritic cells obtained in accordance with the protocols of Example 1 were added to C57BL/6 mouse lymphocytes. The percentage of $CD3^+CD161c^+$ cells in the cell subpopulation was measured on day 14 of culture. It can be seen from FIG. 7 that the addition of semi-allogeneic mouse dendritic cells (shown as "Semi-allogeneic cells" in the Figure) can efficiently promote the increase in the proportion of $CD8^+$ NKT-like cells compared to the allogeneic mouse dendritic cells (shown as "Allogeneic cells" in the Figure).

Figure 8:
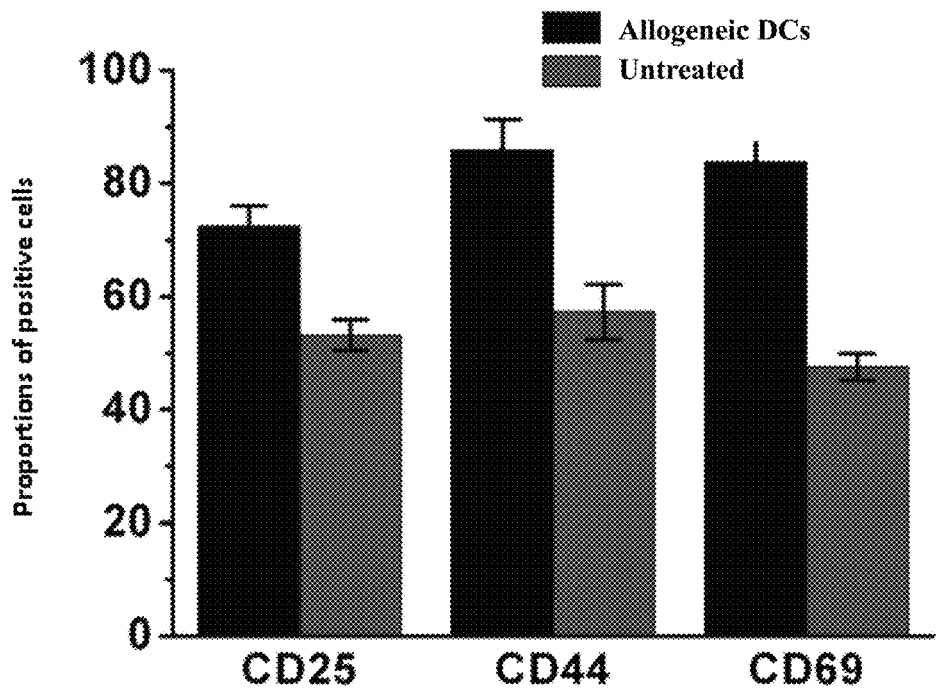
FIG. 8 illustrates the change of the proportions of the activated cells in the culture system of the mouse spleen cells after challenged by allogeneic (mouse) nucleated somatic cells (dendritic cells) in vitro.

FIG. 8 illustrates the change of the proportions of the activated cells in the culture system of the mouse spleen cells after challenged by allogeneic (mouse) nucleated somatic cells (dendritic cells) in vitro. Allogeneic (DBA mice) dendritic cells were added to C57BL/6 mouse lymphocytes according to the procedure of Example 5. The percentage of $CD25^+CD44^+CD69^+$ cells in the culture system was measured on day 14 of culture. The expression of CD25/CD44/CD69 molecules is a marker of activated lymphocytes. It can be seen from FIG. 8 that the addition of allogeneic mouse dendritic cells (shown as "Allogeneic DCs" group in the Figure) can efficiently promote the increase in the proportion of activated cells ($CD25^+$ cells, $CD44^+$ cells, $CD69^+$ cells), compared to the group (shown as "Untreated" group in the Figure) in which the allogeneic mouse dendritic cells were not added.

Figure 9:
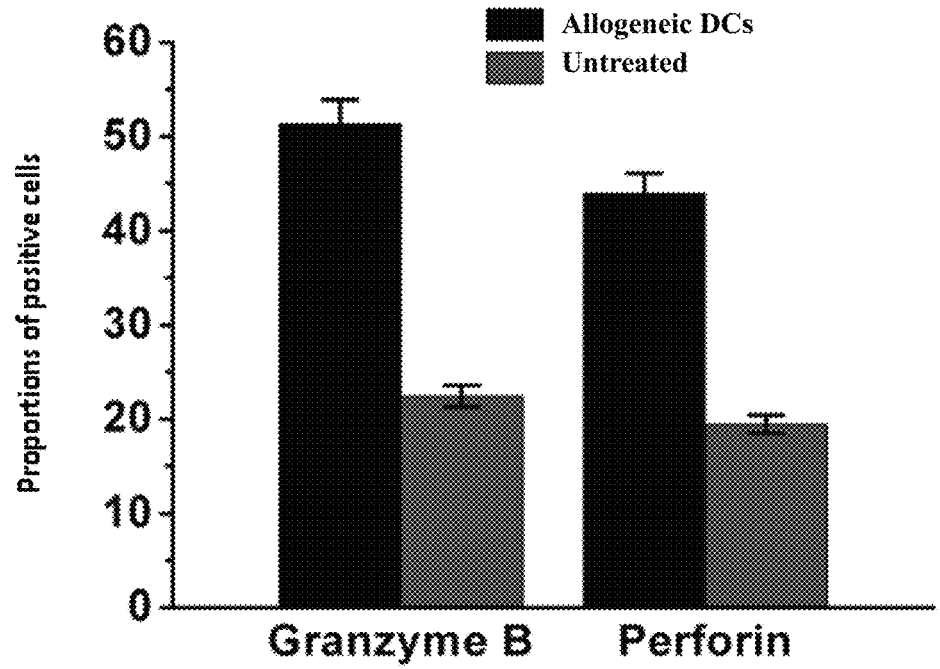
FIG. 9 illustrates the change of the proportions of cells having killing activity in the culture system of the mouse spleen cells after challenged by allogeneic (mouse) nucleated somatic cells (dendritic cells) in vitro.

FIG. 9 illustrates the change of the proportions of cells having killing activity in the culture system of the mouse spleen cells after challenged by allogeneic (mouse) nucleated somatic cells (dendritic cells) in vitro. Allogeneic (DBA mice) dendritic cells were added to C57BL/6 mouse lymphocytes according to the procedure of Example 5. The percentage of Granzyme $B^+$/Perforin$^+$ cells in CD8 T cells was measured on day 14 of culture. Granzyme B and Perforin are molecules involved in a granule release pathway. The high expression of Granzyme B and Perforin indicates that the cell has an ability of killing target cells. It can be seen from FIG. 9 that the addition of allogeneic dendritic cells (shown as "Allogeneic DCs" group in the Figure) can efficiently promote the expression of Granzyme B and Perforin, compared to the group (shown as "Untreated" group in the Figure) in which the allogeneic dendritic cells were not added.

The disclosure is further described by the following examples, but the examples are only used for the purpose of illustrating the invention rather than limiting the scope of the invention. Other embodiments will be apparent to a person skilled in the art when reading the specification with reference to the common knowledge.

The following experimental methods described in the examples are the conventional methods unless specifically stated. The experimental materials used in the following examples are available from the commercial companies unless specifically stated. In addition, the specific experimental conditions not specified in the following examples may be referred to the conditions described in experimental reference books or the recommended conditions provided by the suppliers. Unless otherwise stated, the percentage is a mass to volume ratio.

EXAMPLES

Example 1: The Detection of the Phenotype of Mouse CD8⁺ NKT-like Cells (1) C57BL/6 mouse spleen cells were isolated, and mononuclear cells were separated from the spleen cells by density gradient centrifugation with Ficoll medium having a density of 1.083.
(2) PanNK positive cells were sorted out from the mouse spleen cells according to the requirement of panNK Positive Sorting Kit available from Stemcell Inc. The experimental steps were specifically listed as follows:
i) the spleen mononuclear cells were resuspended in PBS buffer to $10^8$/mL;
ii) CD49b-PE (CD49b is a marker of panNK positive cells) was added in an amount of 50 µL/mL cell suspension, and incubated away from light at room temperature for 15 minutes;
iii) a cocktail liquid was added in an amount of 100 µL/mL cell suspension, and incubated away from light at room temperature for 15 minutes;
iv) magnetic beads were added in an amount of 50 µL/mL cell suspension, and incubated away from light at room temperature for 10 minutes;
v) PBS was added to the cell suspension to reach a total volume of 2.5 mL, and then the resulting cell suspension was transferred to a 5 mL BD Falcon flow cytometry injection tube which was subsequently placed in a Stemcell positive sorting magnet and let stand for 5 minutes;
vi) the magnet was picked up and the negative cells were discarded;
vii) the cell pellet was resuspended in 2.5 mL PBS, and the resulting cell suspension was placed in a Stemcell positive sorting magnet and let stand for 5 minutes;
viii) the magnet was picked up and the negative cells were discarded; and
ix) the BD Falcon flow cytometry injection tube was taken from the magnet, and the positive cells were resuspended in 500 µL PBS.
(3) The positive cells were resuspended in 200 µL PBS, labeled with 10 µL APC labeled α-GalCer-loaded CD1d tetramer (Proimmune Inc.), and then incubated at 4° C. for 30 minutes.
(4) The cells were washed one time with 1 mL PBS. The cells were resuspended in 500 µL PBS, and labeled after subpackaged in tubes at 50 µL/tube (note: all fluorescent antibodies were purchased from BioLegend Inc., unless specifically stated):
Tube 1 was used to label TCRβ-FITC, CD8-PerCP, CD3-APC-Cy7, NK1.1-PE-Cy7.
Tube 2 was used to label TCRβ-FITC, CD8-APC-Cy7, NKG2D-PE-Cy7, CD44-PerCP.
Tube 3 was used to label TCRβ-APC-Cy7, CD8-PerCP, KLRG1-PE-Cy7, Ly49G2-FITC (eBioscience Inc.).
Tube 4 was used to label TCRβ-APC-Cy7, CD8-PerCP, CD27-PE-Cy7, NKG2A/C/E-FITC.
Tube 5 was used to label TCRβ-APC-Cy7, CD8-PE-Cy7, CD62L-FITC, CD122-PerCP.

Tubes 6-10 were used to label corresponding isotype control antibodies of the above-mentioned antibodies (available from BioLegend Inc.).
(5) Each sample tube was incubated at 4° C. for 30 minutes.
(6) Each sample tube was added 1 mL PBS, centrifuged at 1500 rpm for 10 minutes, and the supernatant was discarded.
(7) Step (6) was repeated, and the cell pellet was resuspended in 300 µL PBS.
(8) The cell suspension was loaded on a BD FACSAria II flow cytometry. The detection of CD8⁺DX5⁺TCRβ⁺CD1d Tetramer⁻ cells (mouse CD8⁺ NKT-like cells) was performed.
The results showed that the mouse CD8⁺ NKT-like cells expressed T cell lineage marker CD3 and TCRβ as well as NK cell lineage marker NK1.1(CD161c), but did not express iNKT lineage marker CD1d. In addition, it can also be seen from FIG. 1 that the CD8⁺ NKT-like cells disclosed herein expressed T cell activation markers (CD44. CD62L and CD122) as well as NK cell receptors (NKG2A/C/E, KLRG1, NKG2D, Ly49G$_2$ and CD27).

Example 2: Phenotypic Differences Between Mouse CD8⁺ NKT-like Cells Disclosed Herein and Mouse NK Cells, Mouse iNKT Cells and Mouse CTL Cells (1) C57BL/6 mouse spleen cells were isolated, and mononuclear cells were separated from the spleen cells by density gradient centrifugation with Ficoll medium having a density of 1.083.
(2) PanNK positive cells were sorted out from the mouse spleen cells according to the requirement of panNK Positive Sorting Kit available from Stemcell Inc. The experimental steps were specifically listed as follows:
i) the spleen mononuclear cells were resuspended in PBS buffer to $10^8$/mL;
ii) CD49b-PE (CD49b is a marker of panNK positive cells) was added in an amount of 50 µL/mL cell suspension, and incubated away from light at room temperature for 15 minutes;
iii) a cocktail liquid was added in an amount of 100 µL/mL cell suspension, and incubated away from light at room temperature for 15 minutes;
iv) magnetic beads were added in an amount of 50 µL/mL cell suspension, and incubated away from light at room temperature for 10 minutes;
v) PBS was added to the cell suspension to reach a total volume of 2.5 mL, and then the resulting cell suspension was transferred to a 5 mL BD Falcon flow cytometry injection tube which was subsequently placed in a Stemcell positive sorting magnet and let stand for 5 minutes;
vi) the magnet was picked up and the negative cells were poured into a new centrifuge tube;
vii) the cell pellet was resuspended in 2.5 mL PBS, and the resulting cell suspension was placed in a Stemcell positive sorting magnet and let stand for 5 minutes;
viii) the magnet was picked up and the negative cells were discarded; and
ix) the BD Falcon flow cytometry injection tube was taken from the magnet, and the positive cells were resuspended in 500 µL PBS.
(3) The positive cells were resuspended in 200 µL PBS, labeled with 10 µL APC labeled α-GalCer-loaded CD1d tetramer (Proimmune Inc.), and then incubated at 4° C. for 30 minutes.

(4) The cells were washed one time with 1 mL PBS. The cells were resuspended in 500 μL PBS, and labeled after subpackaged in tubes at 50 μL/tube (all purchased from BioLegend Inc.):

Tube 1 was used to label TCRβ-FITC, CD8-PerCP, CD3-APC-Cy7, NK1.1-PE-Cy7.

Tube 2 was used to label TCRβ-FITC, CD8-APC-Cy7, NKG2D-PE-Cy7.

Tube 3 was used to label TCRβ-APC-Cy7, CD8-PerCP, KLRG1-PE-Cy7, Ly6G-FITC.

Tube 4 was used to label TCRβ-APC-Cy7, CD8-PerCP, CD27-PE-Cy7, NKG2A/C/E-FITC.

Tubes 5-8 were used to label corresponding isotype control antibodies of the above-mentioned antibodies (available from BioLegend Inc.).

(5) Each sample tube was incubated at 4° C. for 30 minutes.
(6) Each sample tube was added 1 mL PBS, centrifuged at 1500 rpm for 0 minutes, and the supernatant was discarded.
(7) Step (6) was repeated, and the cell pellet was resuspended in 300 μL PBS.
(8) The cell suspension was loaded on a BD FACSAria II flow cytometry. CD8$^+$DX5$^+$TCRβ$^+$CD1d Tetramer$^-$ cells (mouse CD8$^+$ NKT-like cells), CD8$^-$DX5$^+$TCRβ$^+$CD1d Tetramer$^+$ cells (mouse iNKT cells), CD8$^+$DX5$^-$TCRβ$^+$CD1d Tetramer$^-$ cells (mouse CD8$^+$ T cells), and DX5$^+$TCRβ$^-$ cells (mouse NK cells) were gated to analyze these phenotypes.

The results showed that there are phenotypic differences between the CD8$^+$ NKT-like cells disclosed herein and NK cells, iNKT cells and CTL cells in mice. It can be seen from FIG. 2 that: (1) compared with NK cells, the CD8$^+$ NKT-like cells expressed not only NK cell markers [NK1.1 (CD161c), NKG2A/C/E, CD27, KLRG1 and Ly6G], but also TCRβ and CD3 which were not expressed on the NK cells; (2) compared with CTL cells, the CD8$^+$ NKT-like cells expressed T cell lineage markers (TCRβ and CD3), but did not express NK cell receptors; (3) compared with iNKT cells, the CD8$^+$ NKT-like cells cannot bind to the CD1d tetramer loaded with lipid antigens.

Example 3 Preparation of Mouse Nucleated Somatic Cells (1) Preparation of Dendritic Cells Induced In Vitro:
C57BL/6 mouse femur marrow hematopoietic precursor cells were taken and added with 50 ml 1640 culture medium comprising 100 ng/ml granulocyte/monocyte colony stimulating factor (GM-CSF), 50 ng/ml interleukin 4 (IL-4), 50 ng/ml tumor necrosis factor α (TNF-α), and 10% fetal bovine serum. After cultured for 7 days in vitro, 5 ng/ml LPS was added for 24 hours to obtain mature mouse dendritic cells.

The cell morphology was shown in FIG. 3. The results obtained by the detection of flow cytometry showed that the cell expressed Ia, CD40, CD80, CD86 and CD11c, which are phenotypes of a mature dendritic cell (see FIG. 4).

(2) Preparation of Activated B Lymphocytes In Vitro:
Freshly isolated C57BL/6 mouse spleen cells were cultured in 1640 culture medium comprising 10% fetal bovine serum, 10 ng/ml mouse IL-6, 10 ng/ml IL-4 and 5 ng/ml LPS at a density of 5×10$^6$/ml for 72 hours to obtain activated B lymphocytes.

(3) Preparation of Mouse Macrophages:
① C57BL/6 mice was anesthetized or sacrificed, and abdominal skin was incised to expose peritoneum;

② 5 ml cold PBS buffer was injected intraperitoneally into mouse abdominal cavity, and peritoneal lavage fluid was collected after repetitively pipetted;

③ After the peritoneal lavage fluid was centrifuged and counted, a magnetic sorting system was used to sort out target cells with CD11b magnetic beads. The positive cells, that is, mouse macrophages, were then harvested.

Example 4 Preparation of Ethanol-fixed Nucleated Somatic Cells (1) Human or animal nucleated somatic cells (e.g., the nucleated somatic cells prepared in Example 3) were prepared;
(2) The cells obtained in step (1) were resuspended in physiological saline at a density of 5×10$^7$/ml, added with ethanol to reach a final concentration of 50% ethanol, and incubated at 4° C. for 15 minutes;
(3) After centrifuged at 700 g for 10 minutes, the supernatant was discarded. The cell pellet was resuspended in 50 ml physiological saline, and kept for 5 minutes;
(4) Step (3) was repeated twice;
(5) After resuspended in 10 ml physiological saline, the cells were cryopreserved at −80° C. for further use.

Example 5 Activation of CD8$^+$ NKT-like Cells by Mouse Allogeneic Nucleated Somatic Cells In Vitro (1) Freshly isolated C57BL/6 mouse spleen cells were resuspended at 5×10$^6$/ml in 1640 culture medium supplemented with 100 IU/ml interleukin 2 and 10% fetal bovine serum, and seeded in 24-well cell culture plates at 1 ml/well; added with 5×10$^4$ DBA/2 mouse dendritic cells;
(2) On day 7 of culture, 5×10$^4$ DBA/2 mouse dendritic cells were added;
(3) On day 14 of culture, cells were collected. The grouping of the cultured cells was performed via a flow cytometry. The results showed that the proportion of CD3$^+$CD161c$^+$ cells in the culture system after challenged was higher than that before challenge (see FIG. 5). At the same time, the proportions of CD25$^+$ cells, CD44$^+$ cells and CD69$^+$ cells in the culture system (see FIG. 8), and the proportions of Granzyme B$^+$ cells and Perforin$^+$ cells (see FIG. 9) were measured by a flow cytometry.

Example 6 Activation of Mouse CD8$^+$ NKT-like Cells In Vitro by Rat Nucleated Somatic Cells (Xenogeneic Cells)

(1) Freshly isolated C57BL/6 mouse spleen cells were resuspended at 5×10$^6$/ml in 1640 culture medium supplemented with 100 IU/ml interleukin 2 and 10% fetal bovine serum, and seeded in 24-well cell culture plates at 1 ml/well; added with 5×10$^4$ Lewis rat peritoneal macrophages;
(2) On day 7 of culture, 5×10$^4$ Lewis rat peritoneal macrophages were added;
(3) On day 14 of culture, cells were collected. The grouping of the cultured cells was performed via a flow cytometry. The results showed that the proportion of CD3$^+$CD161c$^+$ cells in the culture system after challenged was higher than that before challenge (see FIG. 6).

Example 7 Activation of Mouse CD8$^+$ NKT-like Cells In Vitro by Semi-allogeneic Mouse Nucleated Somatic Cells (1) Freshly isolated C57BL/6 mouse spleen cells were resuspended at 5×10$^6$/ml in 1640 culture medium supplemented with 100 IU/ml interleukin 2 and 10% fetal bovine serum, and seeded in 24-well cell culture plates at 1 ml/well; added with $5 \times 10^4$ dendritic cells of a F1 hybrid mice of C57BL/6 mice and DBA/2 mice;

(2) On day 7 of culture, $5 \times 10^4$ dendritic cells of a F1 hybrid mice of C57BL/6 mice and DBA/2 mice were added;

(3) On day 14 of culture, cells were collected. The grouping of the cultured cells was performed via a flow cytometry. The results showed that the proportion of $CD3^+$ $CD161c^+$ cells in the culture system after challenged by semi-allogeneic mouse dendritic cells was higher than that challenged by DBA/2 mouse dendritic cells (see FIG. 7).

The present disclosure provides the following embodiments:

1. A method for activating and expanding NKT-like cells in vitro, comprising the steps of:

1) providing and culturing lymphocytes obtained from a first subject;

2) providing nucleated somatic cells obtained from a second subject;

3) adding the nucleated somatic cells of the second subject to the culture of the lymphocytes of the first subject, and continuously culturing the resulting mixed culture for a period sufficient to expand the number of the lymphocytes by at least 10 to 1000 times; and 4) sorting out NKT-like cells or a subpopulation rich in NKT-like cells from the lymphocytes;

wherein the NKT-like cells express CD8 molecule on their cell surface, and the nucleated somatic cells express immune co-stimulatory molecules on their cell surface; the second subject and the first subject are allogeneic or heterogeneous mammals.

2. The method according to Embodiment 1, wherein the lymphocytes of the first subject and the nucleated somatic cells of the second subject express different types of MHC class I molecules.

3. The method according to Embodiment 1 or 2, wherein the nucleated somatic cell is an immune cell or a non-immune cell.

4. The method according to Embodiment 3, wherein the non-immune cell is a fibroblast.

5. The method according to Embodiment 3, wherein the immune cell is an antigen presenting cell.

6. The method according to Embodiment 5, wherein the antigen presenting cell is any one selected from the group comprising an endothelial cell, a dendritic cell and a B cell, preferably a dendritic cell.

7. The method according to Embodiment 3, wherein the antigen presenting cell is any one selected from the group comprising a granulocyte, a T cell, a B cell, a macrophage, a NK cell, a NKT cell and a NKT-like cell, preferably a macrophage, a B cell or a NKT-like cell.

8. The method according to any one of Embodiments 1 to 7, wherein the NKT-like cell expresses CD3 and CD56 on the cell surface, but not Vα24 TCR.

9. The method according to any one of Embodiments 1 to 7, wherein the NKT-like cell expresses CD3 and CD161c on the cell surface, but not Vα14 TCR.

10. The method according to Embodiment 8 or 9, wherein the NKT-like cell also expresses TCRαβ on the cell surface.

11. The method according to any one of Embodiments 1 to 10, wherein the immune co-stimulatory molecule is any one selected from the group comprising CD40, CD80 and CD86, or any combination thereof.

12. The method according to any one of Embodiments 1 to 11, wherein the mammal is selected from the group consisting of bovidae, equidae, felidae, canidae, leporidae, suidae, camelidae, rodent and primate, preferably a cattle, a horse, a dog, a goat, a sheep, a cat, a rabbit, a pig, a camel, an alpaca, a rat, a mouse, a guinea pig, a non-human primate or a human, more preferably a cattle, a horse, a dog, a goat, a sheep, a pig, a camel, a rat, a mouse, a monkey or a human.

13. The method according to any one of Embodiments 1 to 12, wherein the second subject and the first subject are semi-allogeneic individuals.

14. The method according to any one of Embodiments 1 to 13, wherein the second subject and the first subject are heterogeneous individuals.

15. The method according to any one of Embodiments 1 to 14, wherein prior to the step 3), the nucleated somatic cells of the second subject obtained in the step 2) are incubated with a tumor antigen so that the nucleated somatic cells phagocytose the tumor antigen.

16. The method according to any one of Embodiments 1 to 15, wherein prior to the step 3), the nucleated somatic cells of the second subject obtained in the step 2) are subjected to any one selected from the following treatments: heat inactivation, radiation inactivation, chemical reagent fixation, frozen treatment and ultrasonic cleavage treatment.

17. The method according to any one of Embodiments 1 to 16, wherein in the step 3), the nucleated somatic cells are added to the culture of the lymphocytes at a ratio of the nucleated somatic cells to the lymphocytes of 1:1000 to 1:1, preferably 1:100 to 1:1, more preferably 1:10 to 1:1, and most preferably 1:1.

18. The method according to any one of Embodiments 1 to 17, wherein the nucleated somatic cells are freshly isolated from the second subject, or the nucleated somatic cell is an established cell line obtained after a long-term culture of the isolated nucleated somatic cells.

19. The method according to any one of Embodiments 1 to 18, wherein prior to the step 3), cytokines may be added to the culture of the nucleated somatic cells obtained in the step 2) to expand or activate the nucleated somatic cells.

20. The method according to Embodiment 19, wherein the cytokine is selected from the group consisting of growth factors such as fibroblast growth factor, endothelial cell growth factor, granulocyte/monocyte colony stimulating factor, or activating factors such as tumor necrosis factor alpha, or any combination thereof.

21. The method according to any one of Embodiments 1 to 20, wherein the method further comprises:

5) adding a cytokine capable of stimulating T cell proliferation and activation to a culture of the NKT-like cells or a subpopulation rich in the NKT-like cells sorted out in the step 4), thereby further expanding the NKT-like cells by 10 to 1000 times.

22. The method according to Embodiment 21, wherein the cytokine is one selected from the group consisting of GM-CSF, IL-2, IL-4, IL-5, IL-6, IL-7, IL-9, IL-12, IL-15 and 4-1BBL, or any combination thereof.

23. The method according to any one of Embodiments 1 to 22, wherein the expression of lymphocyte activation markers on the NKT-like cell is increased.

24. The method according to Embodiment 23, wherein the lymphocyte activation marker is one selected from the group consisting of CD25, CD44 and CD69, or any combination thereof.

25. The method according to any one of Embodiments 1 to 22, wherein the expression of the killing effector molecule on the NKT-like cell is increased.

26. The method according to Embodiment 25, wherein the killing effector molecule is one selected from the group consisting of Granzyme B, Perforin, and a combination thereof.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCES

[1] Budd, R. C., Miescher, G. C., Howe, R. C., Lees, R. K., Bron, C. and MacDonald, H. R., Developmentally regulated expression of T cell receptor beta chain variable domains in immature thymocytes. J Exp Med 1987. 166: 577-582.
[2] Fowlkes, B. J., Kruisbeek, A. M., Ton-That, H., Weston, M. A., Coligan, J. E., Schwartz, R. H. and Pardoll, D. M., A novel population of T-cell receptor alpha beta-bearing thymocytes which predominantly expresses a single V beta gene family. Nature 1987. 329: 251-254.
[3] Ceredig, R., Lynch, F. and Newman, P., Phenotypic properties, interleukin 2 production, and developmental origin of a "mature" subpopulation of Lyt-2-L3T4-mouse thymocytes. Proc Natl Acad Sci USA 1987. 84: 8578-8582.
[4] Sykes, M., Unusual T cell populations in adult murine bone marrow. Prevalence of CD3+CD4−CD8− and alpha beta TCR+NK1.1+ cells. J Immunol 1990. 145: 3209-3215.
[5] Makino, Y, Kanno, R., Ito, T., Higashino, K. and Taniguchi, M., Predominant expression of invariant V alpha 14+ TCR alpha chain in NK1.1+ T cell populations. Int Immunol 1995. 7: 1157-1161.
[6] Godfrey, D. I., MacDonald, H. R., Kronenberg, M., Smyth, M. J. and Van Kaer, L., NKT cells: what's in a name? Nat Rev Immunol 2004. 4: 231-237.
[7] Maeda, M., Shadeo, A., MacFadyen, A. M. and Takei, F., CD1d-independent NKT cells in beta 2-microglobulin-deficient mice have hybrid phenotype and function of NK and T cells. J Immunol 2004. 172: 6115-6122.

What is claimed is:

1. A method for activating and expanding NKT-like cells in vitro, comprising the steps of:
   1) providing and culturing lymphocytes obtained from a first subject;
   2) providing nucleated somatic cells obtained from a second subject;
   3) adding the nucleated somatic cells of the second subject to the culture of the lymphocytes of the first subject, and continuously culturing the resulting mixed culture for a period sufficient to expand the number of the lymphocytes by at least 10 to 1000 times; and
   4) sorting out NKT-like cells or a subpopulation rich in NKT-like cells from the lymphocytes with the surface markers of the NKT-like cell;
   wherein the phenotype of the NKT-like cells is TCRαβ+CD3+CD56+CD8+Vα24 TCR− or TCRαβ+CD3+CD161c+CD8+Vα14 TCR, and the nucleated somatic cells express immune co-stimulatory molecules on their cell surface; the second subject and the first subject are allogeneic or heterogeneous mammals, and
   wherein the surface markers of the NKT-like cell comprise CD8, CD3, TCRαβ, CD161c, CD44, CD62L, CD122, NKG2A/C/E, KLRG1, NKG2D, Ly49G2 and CD27, or comprise CD8, CD3 TCRαβ, CD56, CD44, CD62L, CD122, NKG2A/C/E, KLRG1, NKG2D, Ly49G2 and CD27.

2. The method according to claim 1, wherein the lymphocytes of the first subject and the nucleated somatic cells of the second subject express different types of MHC class I molecules.

3. The method according to claim 1, wherein the nucleated somatic cell is an immune cell.

4. The method according to claim 3, wherein the immune cell is any one selected from the group consisting of a granulocyte, a T cell, a B cell, a macrophage, a NK cell, a NKT cell and a NKT-like cell, preferably a macrophage, a B cell or a NKT-like cell.

5. The method according to claim 3, wherein the immune cell is an antigen presenting cell.

6. The method according to claim 5, wherein the antigen presenting cell is any one selected from the group consisting of an endothelial cell, a dendritic cell and a B cell, preferably a dendritic cell.

7. The method according to claim 1, wherein the immune co-stimulatory molecule is any one selected from the group consisting of CD40, CD80 and CD86, or any combination thereof.

8. The method according to claim 1, wherein the second subject and the first subject are semi-allogeneic individuals or heterogeneous individuals.

9. The method according to claim 1, wherein prior to the step 3), the nucleated somatic cells of the second subject obtained in the step 2) are incubated with a tumor antigen so that the nucleated somatic cells phagocytose the tumor antigen.

10. The method according to claim 1, wherein prior to the step 3), the nucleated somatic cells of the second subject obtained in the step 2) are subjected to any one selected from the following treatments: heat inactivation, radiation inactivation, chemical reagent fixation, frozen treatment and ultrasonic cleavage treatment.

11. The method according to claim 1, wherein in the step 3), the nucleated somatic cells are added to the culture of the lymphocytes at a ratio of the nucleated somatic cells to the lymphocytes of 1:1000 to 1:1, preferably 1:100 to 1:1, more preferably 1:10 to 1:1, and most preferably 1:1.

12. The method according to claim 1, wherein prior to the step 3), cytokines are added to the culture of the nucleated somatic cells obtained in the step 2) to expand or activate the nucleated somatic cells, and the cytokine is selected from the group consisting of a growth factor, an activating factor, or any combination thereof.

* * * * *